(12) United States Patent
Kitching et al.

(10) Patent No.: US 10,052,174 B2
(45) Date of Patent: *Aug. 21, 2018

(54) TREATMENT PROGRESS TRACKING AND RECALIBRATION

(71) Applicant: Align Technology, Inc., San Jose, CA (US)

(72) Inventors: Ian Kitching, Saratoga, CA (US); Rene Sterental, Palo Alto, CA (US); Eric Kuo, San Jose, CA (US); Maia Singer, Campbell, CA (US)

(73) Assignee: Align Technology, Inc., San Jose, CA (US)

( * ) Notice: Subject to any disclaimer, the term of this patent is extended or adjusted under 35 U.S.C. 154(b) by 286 days.

This patent is subject to a terminal disclaimer.

(21) Appl. No.: 14/665,926

(22) Filed: Mar. 23, 2015

(65) Prior Publication Data

US 2015/0190212 A1    Jul. 9, 2015

Related U.S. Application Data

(63) Continuation of application No. 14/341,645, filed on Jul. 25, 2014, now Pat. No. 9,017,072, which is a
(Continued)

(51) Int. Cl.
*A61C 3/00* (2006.01)
*A61C 7/00* (2006.01)
*A61C 7/08* (2006.01)

(52) U.S. Cl.
CPC ............... *A61C 7/00* (2013.01); *A61C 7/002* (2013.01); *A61C 7/08* (2013.01)

(58) Field of Classification Search
CPC .. A61C 7/002; A61C 7/00; A61C 7/08; A61C 7/146
(Continued)

(56) References Cited

U.S. PATENT DOCUMENTS 2,467,432 A   4/1949   Kesling
3,407,500 A   10/1968  Kesling
(Continued)

FOREIGN PATENT DOCUMENTS

AU    3031677 A    5/1979
AU    517102 B2    7/1981
(Continued)

OTHER PUBLICATIONS

AADR. American Association for Dental Research, Summary of Activities, Mar. 20-23, 1980, Los ngeles, CA, p. 195.
(Continued)

*Primary Examiner* — Matthew Nelson
(74) *Attorney, Agent, or Firm* — Wilson Sonsini Goodrich & Rosati

(57) ABSTRACT

The present invention relates to systems and methods of developing and tracking delivery and patient progression through an orthodontic treatment plan. One method includes identifying deviations from an orthodontic treatment plan, including receiving a digital representation of an actual arrangement of a patient's teeth after an orthodontic treatment plan has begun for the patient and prior to completion of the orthodontic treatment plan. The method further includes comparing the actual arrangement to a pre-determined planned arrangement to determine if the actual arrangement substantially deviates from the planned arrangement, the comparing comprising matching teeth from a previously segmented model to a surface of an unsegmented representation of the actual arrangement; and calculating one or more positional differences between the actual and planned arrangements of at least some of the corresponding teeth.

19 Claims, 11 Drawing Sheets

Related U.S. Application Data continuation of application No. 14/034,373, filed on Sep. 23, 2013, now Pat. No. 8,899,978, which is a continuation of application No. 11/760,705, filed on Jun. 8, 2007, now Pat. No. 8,562,338.

(58) Field of Classification Search
USPC .......................... 433/24, 215; 705/3; 700/98
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,431,562 A | 11/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,752,832 A | 5/1998 | Vardimon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,067,523 A | 5/2000 | Bair et al. |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordon et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 * | 11/2001 | Sachdeva ............... A61C 7/00 433/213 |
| 6,322,359 B1 | 11/2001 | Jordan et al. |
| 6,350,120 B1 | 2/2002 | Sachdeva et al. |
| 6,382,975 B1 | 5/2002 | Poirier |

(56) References Cited

U.S. PATENT DOCUMENTS

| | | |
|---|---|---|
| 6,398,548 B1 | 6/2002 | Muhammad et al. |
| 6,402,707 B1 | 6/2002 | Ernst |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 7,074,038 B1 | 7/2006 | Miller |
| 7,077,647 B2 | 7/2006 | Choi et al. |
| 7,156,661 B2 | 1/2007 | Choi et al. |
| 7,357,636 B2* | 4/2008 | Hedge ............. A61C 7/08 433/24 |
| 7,474,307 B2 | 1/2009 | Chishti et al. |
| 8,075,306 B2 | 12/2011 | Kitching et al. |
| 8,562,338 B2 | 10/2013 | Kitching et al. |
| 8,636,510 B2 | 1/2014 | Kitching et al. |
| 8,899,978 B2 | 12/2014 | Kitching et al. |
| 9,017,072 B2 | 4/2015 | Kitching et al. |
| 9,060,829 B2 | 6/2015 | Sterental et al. |
| 9,364,297 B2 | 6/2016 | Kitching et al. |
| 2001/0002310 A1 | 5/2001 | Chishti et al. |
| 2002/0006597 A1 | 1/2002 | Andreiko et al. |
| 2002/0010568 A1 | 1/2002 | Rubbert et al. |
| 2002/0064746 A1 | 5/2002 | Muhammad et al. |
| 2002/0072027 A1 | 6/2002 | Chishti |
| 2003/0009252 A1 | 1/2003 | Pavlovskaia et al. |
| 2003/0139834 A1 | 7/2003 | Nikolskiy et al. |
| 2003/0143509 A1 | 7/2003 | Kopelman et al. |
| 2003/0190575 A1 | 10/2003 | Hilliard |
| 2003/0224311 A1 | 12/2003 | Cronauer |
| 2004/0072120 A1 | 4/2004 | Lauren |
| 2004/0128010 A1 | 7/2004 | Pavlovskaia et al. |
| 2004/0197727 A1 | 10/2004 | Sachdeva et al. |
| 2004/0202983 A1 | 10/2004 | Tricca et al. |
| 2005/0038669 A1 | 2/2005 | Sachdeva et al. |
| 2005/0048432 A1* | 3/2005 | Choi ............. A61C 7/002 433/24 |
| 2005/0055118 A1 | 3/2005 | Nikolskiy et al. |
| 2005/0089822 A1 | 4/2005 | Geng et al. |
| 2005/0192835 A1 | 9/2005 | Kuo et al. |
| 2005/0241646 A1 | 11/2005 | Sotos et al. |
| 2005/0271996 A1 | 12/2005 | Sporbert et al. |
| 2006/0004609 A1 | 1/2006 | Kenneth et al. |
| 2006/0079981 A1* | 4/2006 | Rubbert ............. A61C 7/00 700/98 |
| 2006/0121408 A1 | 6/2006 | Hedge et al. |
| 2006/0127836 A1* | 6/2006 | Wen ............. A61C 7/00 433/24 |
| 2006/0147872 A1 | 7/2006 | Andreiko |
| 2006/0194163 A1 | 8/2006 | Tricca et al. |
| 2006/0199142 A1 | 9/2006 | Liu et al. |
| 2006/0263739 A1* | 11/2006 | Sporbert ............. A61C 7/00 433/24 |
| 2006/0286501 A1 | 12/2006 | Chishti et al. |
| 2007/0003900 A1* | 1/2007 | Miller ............. A61C 7/00 433/24 |
| 2007/0072144 A1* | 3/2007 | Imgrund ............. A61C 7/00 433/24 |
| 2007/0099147 A1* | 5/2007 | Sachdeva ............. A61C 7/00 433/24 |
| 2007/0184398 A1 | 8/2007 | Cronauer |
| 2007/0226005 A1 | 9/2007 | Smith et al. |
| 2008/0050692 A1 | 2/2008 | Hilliard |
| 2008/0305452 A1 | 12/2008 | Sterental et al. |
| 2008/0305453 A1 | 12/2008 | Kitching et al. |
| 2008/0305454 A1 | 12/2008 | Kitching et al. |
| 2008/0306724 A1 | 12/2008 | Kitching et al. |
| 2012/0225401 A1 | 9/2012 | Kitching et al. |
| 2014/0023980 A1 | 1/2014 | Kitching et al. |
| 2014/0193765 A1 | 7/2014 | Kitching et al. |
| 2014/0335466 A1 | 11/2014 | Kitching et al. |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 0091876 A1 | 7/2000 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO-2006118771 A2 | 11/2006 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 2225, 1996, Springer-Verlag, pp. 511-520.

Alexander et al., "The DigiGraph Work Station Part 2 Clinical Management," JCO, pp. 402-407 (Jul. 1990).

Altschuler et al., "Analysis of 3-D Data for Comparative 3-D Serial Growth Pattern Studies of Oral-Facial Structures," AADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

(56) References Cited

OTHER PUBLICATIONS

Bernard et al., "Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/-pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992.
Definition for gingiva. Dictionary.com p. 1-3. Retrieved from the interne Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
DENT-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret, "Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al. "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

(56) References Cited

OTHER PUBLICATIONS

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances—Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, Am. J. Orthod. Oral Surg. (1946) 32:285-293.

Kleeman et al., The Speed Positioner, J. Clin. Orthod. (1996) 30:673-680.

Kochanek, "Interpolating Splines with Local Tension, Continuity and Bias Control," Computer Graphics, 18(3):33-41 (Jul. 1984). Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus:Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventor's CAD/CAM May Transform Dentistry," Dentist, 3 pages total, Sep. 1990.

Ponitz, "Invisible Retainers," Am. J. Orthod., 59(3):266-272 (Mar. 1971).

PROCERA Research Projects, "PROCERA Research Projects 1993—Abstract Collection," pp. 3-7 28 (1993).

Proffit et al., Contemporary Orthodontics, (Second Ed.), Chapter 15, Mosby Inc., pp. 470-533 (Oct. 1993).

Raintree Essix & ARS Materials, Inc., Raintree Essix, Technical Magazine Table of contents and Essix Appliances, <http://www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow et al. "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording the Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).

Schellhas et al., "Three-Dimensional Computed Tomography in Maxillofacial Surgical Planning," Arch. Otolamp!. Head Neck Surg., 114:438-442 (Apr. 1988).

Schroeder et al., Eds. The Visual Toolkit, Prentice Hall PTR, New Jersey (1998) Chapters 6, 8 & 9, (pp. 153-210,309-354 and 355-428, respectively).

(56) References Cited

OTHER PUBLICATIONS

Shilliday, (1971). Minimizing finishing problems with the mini-positioner, Am. J. Orthod. 59:596-599.
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances-Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); Ill.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); Ill. The General Concept of the D.P. Method and Its Therapeutic Effect, Part 1, Dental and Functional Reversed Occlusion Case Reports," Nippon Dental Review, 457:146-164 (Nov. 1980).
Andrews, The Six Keys to Optimal Occlusion Straight Wire, Chapter 3, pp. 13-24 (1989).
Biostar Opeation & Training Manual. Great Lakes Orthodontics, Ltd. 199 Fire Tower Drive, Tonawanda, New York. 14150-5890, 20 pages total (1990).
Dentrac Corporation, Dentrac document, pp. 4-13 (1992).
DuraClearTM product information, Allesee Orthodontic Appliances-Pro Lab, 1 page (1997).
Rekow et al., "CAD/CAM for Dental Restorations—Some of the Curious Challenges," IEEE Trans. Biomed. Eng., 38(4):314-318 (Apr. 1991).
Siemens, "CEREC—Computer-Reconstruction," High Tech in der Zahnmedizin, 14 pages total (2004).
Tru-Tain Orthodontic & Dental Supplies, Product Brochure, Rochester, Minnesota 55902, 16 pages total (1996).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
You May Be a Candidate for This Invisible No-Braces Treatment, Allesee Orthodontic Appliances-Pro Lab product information for patients, 2 pages (2002).
European search report with written opinion dated Mar. 7, 2017 for EP16197945.5.
Richmond, et al. A 2-Center Comparison of Orthodontist's Perceptions of Orthodontic Treatment Difficulty. Jan. 2001, Angle Orthodontist, vol. 71, No. 5, pp. 404-410.

\* cited by examiner

TREATMENT PROGRESS TRACKING AND RECALIBRATION

CROSS-REFERENCE

This application is a continuation of U.S. patent application Ser. No. 14/341,645, filed Jul. 25, 2014, now U.S. Pat. No. 9,017,072, which is a continuation of U.S. patent application Ser. No. 14/034,373, filed Sep. 23, 2013, now U.S. Pat. No. 8,899,978, issued Dec. 2, 2014, which is a continuation of U.S. patent application Ser. No. 11/760,705, filed Jun. 8, 2007, now U.S. Pat. No. 8,562,338, issued Oct. 22, 2013, the entire contents of each of which are incorporated herein by reference.

This application is related to U.S. patent application Ser. No. 11/760,689, filed Jun. 8, 2007; U.S. patent application Ser. No. 11/760,701, filed Jun. 8, 2007; and U.S. patent application Ser. No. 11/760,612, filed Jun. 8, 2007, now U.S. Pat. No. 8,075,306, issued Dec. 13, 2011; the contents of each of which are incorporated herein by reference.

BACKGROUND OF THE INVENTION

The present invention relates generally to the field of orthodontics, and more particularly to systems and methods of developing and tracking delivery and patient progression through an orthodontic treatment plan.

An objective of orthodontics is to move a patient's teeth to positions where function and/or aesthetics are optimized. Traditionally, appliances such as braces are applied to the patient's teeth by an orthodontist or dentist and the set of braces exerts continual force on the teeth and gradually urges them toward their intended positions. Over time and with a series of clinical visits and adjustments to the braces, the orthodontist adjusts the appliances to move the teeth toward their final destination.

More recently, alternatives to conventional orthodontic treatment with traditional affixed appliances (e.g., braces) have become available. For example, systems including a series of preformed aligners have become commercially available from Align Technology, Inc., Santa Clara, Calif., under the tradename Invisalign® System. The Invisalign® System includes designing and/or fabricating multiple, and sometimes all, of the aligners to be worn by the patient before the aligners are administered to the patient and used to reposition the teeth (e.g., at the outset of treatment). Often, designing and planning a customized treatment for a patient makes use of computer-based 3-dimensional planning/design tools, such as ClinCheck® from Align Technology, Inc. The design of the aligners can rely on computer modeling of a series of planned successive tooth arrangements, and the individual aligners are designed to be worn over the teeth and elastically reposition the teeth to each of the planned tooth arrangements.

While patient treatment and tooth movements can be planned prospectively, in some cases orthodontic treatment can deviate from the planned treatment or stages. Deviations can arise for numerous reasons, and can include biological variations, poor patient compliance, and/or factors related to biomechanical design. In the case of aligners, continued treatment with previously designed and/or fabricated aligners can be difficult or impossible where a patient's teeth deviate substantially from the planned treatment course. For example, subsequent aligners may no longer fit the patient's teeth once treatment progression has deviated from the planned course. Because detecting a deviation from planned treatment most typically relies on visual inspection of the patient's teeth or observation of appliances no longer fitting, treatment can sometimes progress significantly off track by the time a deviation is detected, thereby making any required corrective measures more difficult and/or substantial. Earlier and better off track determinations would, therefore, be beneficial in order to recalibrate the fit of the aligner device on the teeth. Accordingly, improved methods and techniques of detecting and correcting treatment that has deviated from planned or desired treatment course would be desirable, particularly methods allowing early detection of treatment deviation.

SUMMARY OF THE INVENTION

The present invention provides improved systems and methods for tracking a patient's progress according to a planned treatment, incorporating enhanced tracking techniques into treatment delivery and management, and, if necessary, revising or modifying the patient's treatment plan based on a determination that treatment has progressed off track. Information obtained according to the invention techniques can be used, for example, to more actively and/or effectively manage delivery of orthodontic treatment, increasing treatment efficacy and successful progression to the patient's teeth to the desired finished positions.

Thus, in one aspect, the present invention includes systems and methods of identifying deviations from an orthodontic treatment plan. A method can include, for example, receiving a digital representation of an actual arrangement of a patient's teeth after an orthodontic treatment plan has begun for the patient and prior to completion of the orthodontic treatment plan; and comparing the actual arrangement to a pre-determined planned arrangement to determine if the actual arrangement substantially deviates from the planned arrangement, and calculating one or more positional differences between the actual and planned arrangements of at least some of the corresponding teeth.

The present invention further includes systems and methods of managing delivery and patient progression through an orthodontic treatment plan. Such a method can include, for example, providing an initial treatment plan for a patient, providing a set of orthodontic appliances, tracking progression of the patient's teeth along the treatment path, comparing the actual arrangement with a planned arrangement to determine if the actual arrangement of the teeth matches a planned tooth arrangement, and generating a revised treatment plan where it is determined that the actual tooth arrangement deviates from the planned tooth arrangement. In another example, a method can include receiving a digital representation of an actual arrangement of a patient's teeth after an orthodontic treatment plan has begun for the patient and prior to completion of the orthodontic treatment plan; comparing the actual arrangement to a digital model of a planned arrangement, and generating a revised treatment plan.

A system can include a computer coupled to a server, the computer comprising a processor and a computer readable medium comprising instructions which, if executed, cause the computer to: receive a digital representation of an actual arrangement of a patient's teeth after the orthodontic treatment plan has begun for the patient and prior to completion of the orthodontic treatment plan; compare the actual arrangement to a pre-determined planned arrangement; and calculate one or more positional differences between the actual and planned arrangements of at least some of the corresponding teeth; and generate a revised treatment plan.

A system according to another embodiment of the present invention can include a computer coupled to a server, the computer comprising a processor and a computer readable medium comprising instructions which, if executed, cause the computer to generate an initial treatment plan for a patient including enhanced tracking of the patient's treatment progress, provide a set of orthodontic appliances corresponding to a treatment phase, track progression of the patient's teeth along a treatment path, compare the actual arrangement with a planned arrangement, and generate a revised treatment plan where it is determined that the actual tooth arrangement substantially deviates from the planned tooth arrangement.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
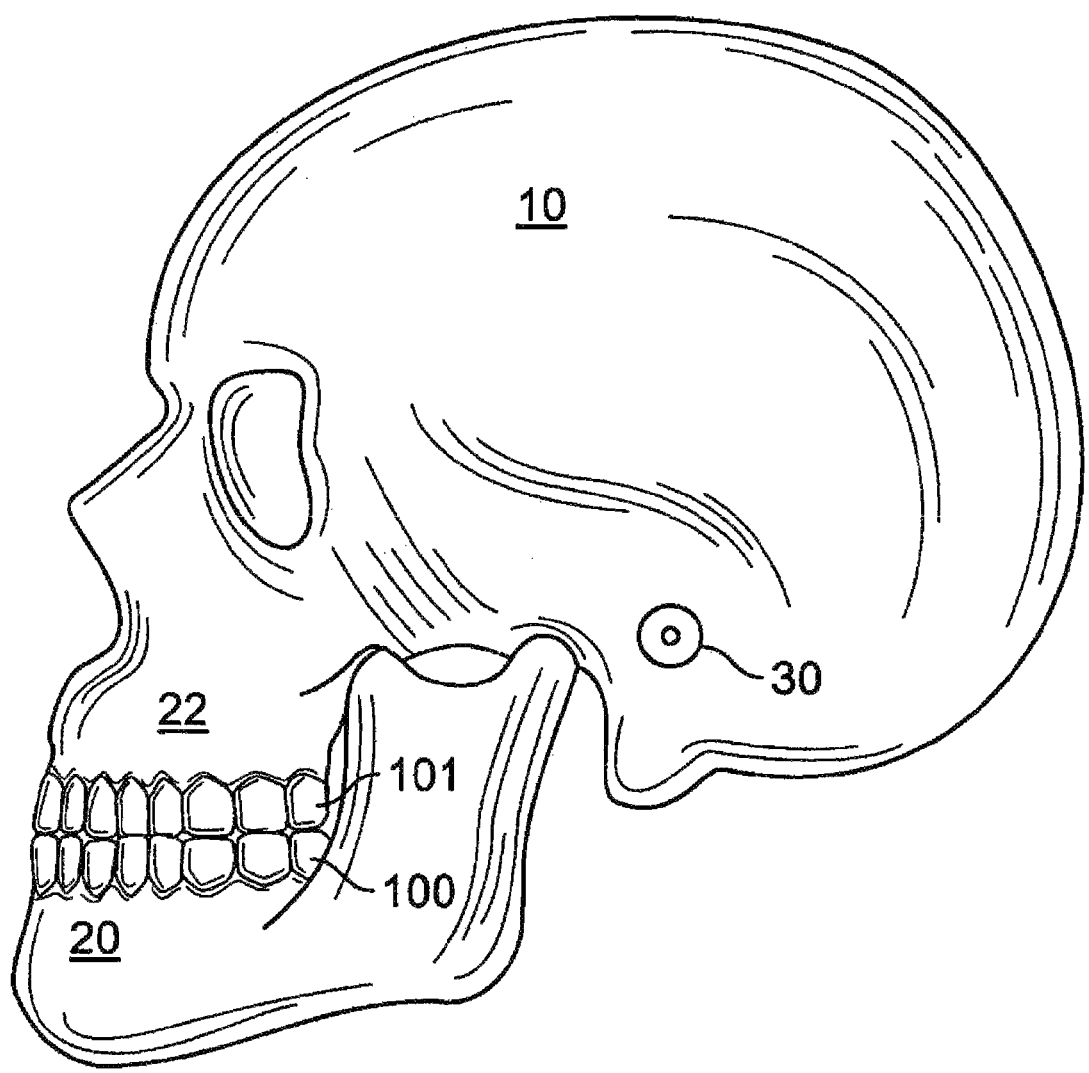
FIG. 1 is a diagram showing the anatomical relationship of the jaws of a patient.

The invention described herein provides improved systems and methods for tracking a patient's progress according to a planned treatment, incorporating enhanced tracking techniques into treatment delivery and management, and, if necessary, revising or modifying the patient's treatment plan based on a determination that treatment has progressed off track. Systems and methods of treatment progress tracking and revised planning can be included in a variety of orthodontic treatment regimens. For example, the progress tracking and revised planning features can be optionally included and incorporated into other aspects of treatment according to the Invisalign® System. Treatment can be pre-planned for administering to a patient in a series of one or more phases, with each phase including a set of appliances that are worn successively by the patient to reposition the teeth through planned arrangements and eventually toward a selected final arrangement. Progress tracking, according to the present invention, is incorporated into the pre-planned treatment for monitoring and management, and to provide enhanced detection and feedback as to whether treatment is progressing on track.

Tracking can occur at any point during treatment but will typically be scheduled to correspond with a patient completing a pre-planned phase of treatment (e.g., wearing each appliance in a designated set). For example, once initial staging of a patients teeth is completed (e.g., model initial, intermediate, and final teeth arrangements) and a treatment plan has been devised, a dental practitioner can be sent a first set of one or more appliances to be administered to the patient in the first phase of treatment. After the last appliance in the first set is administered to the patient, an image of the patient's teeth in their positions following administration of the first set of appliances can be taken (e.g., scan, impression, etc.). From the image of the patient's teeth in their current position, an assessment is made as to how the treatment is tracking relative to the original treatment projections. If there is a substantial deviation from the planned treatment path, then corrective action can be taken, for example, in order to achieve the original designed final position. Treatment then progresses to the next phase, where treatment is either finalized if the intended final positions are reached, or a second set of appliances can be sent to the practitioner for administration to the patient. The second set of appliances can be based on the initial treatment plan if treatment is progressing on track, or can be based on a revised or modified treatment plan where a determination is made that treatment is off track.

Methods and techniques for tracking and preserving the original final position in the treatment is generally referred to herein as "teeth matching" or "bite matching". For example, bite matching techniques described herein can include matching teeth from the original image of the teeth or impression, to surface(s) of a new model of the teeth taken after treatment has begun. An off-track determination can be followed by "re-setting" to the actual position of the teeth as defined by data represented in the progress scan, the original data of the teeth (i.e., segmented models from initial treatment plan), thereby allowing preservation of the initially selected final target position of the teeth. In other words, the original data set which contains with it, an established target arrangement, can be reused, by repositioning the teeth arrangement according to the positions of the (same) teeth captured in the progress scan. In so doing, a new planned path to go from the current to the target can be recreated without having to change the original target configuration. This method is enabled by using bite matching techniques to allow the current aligner geometry to be recalibrated and reshaped according to the actual position of the teeth in the progress scan. Using such bite matching techniques provides significant advantages in terms of efficiency as there is no need to re-segment and process the new scan of the teeth, and in terms of efficacy since the initial final arrangement is preserved, even if the patient progresses off track.

Incorporating the inventive techniques and tracking methods described herein in managing delivery/modification would provide various advantages, including earlier detection of treatment deviations, allowing earlier remedial measures to be taken, if necessary, to avoid undesirable treatment outcomes and preservation of initial treatment goals, thereby ultimately allowing for more effective treatment and better clinical outcomes. Furthermore, treatment efficiency and efficacy can be increased by better avoidance of inefficient/undesirable treatment "detours". Additionally, improved monitoring and tracking, as described, is more objective and reliable, and less qualitative in nature than the common practice of visually identifying off-track progress. This reduces the inter-clinician variability and reduces the dependency of accurate detection on clinician experience. As such, currently described inventive methods and techniques can inspire more confidence in both patients and practitioners, including practitioners that may be less experienced with a given treatment method and/or less confident in their abilities to clinically detect off-track progression, or even more experienced practitioners who desire more detailed monitoring, for example, in cases involving more difficult or less predictable movements.

FIG. 1 shows a skull 10 with an upperjaw bone 22 and a lowerjaw bone 20. The lowerjaw bone 20 hinges at a joint 30 to the skull 10. The joint 30 is called a temporal mandibular joint (TMJ). The upperjaw bone 22 is associated with an upper jaw 101, while the lower jaw bone 20 is associated with a lower jaw 100. A computer model of the jaws 100 and 101 is generated, and a computer simulation models interactions among the teeth on the jaws 100 and 101. The computer simulation allows the system to focus on motions involving contacts between teeth mounted on the jaws. The computer simulation allows the system to render realistic jaw movements that are physically correct when the jaws 100 and 101 contact each other. The model of the jaw places the individual teeth in a treated position. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions are applied to one jaw, but may also be applied to both jaws. Based on the occlusion determination, the final position of the teeth can be ascertained.

Figure 2A:
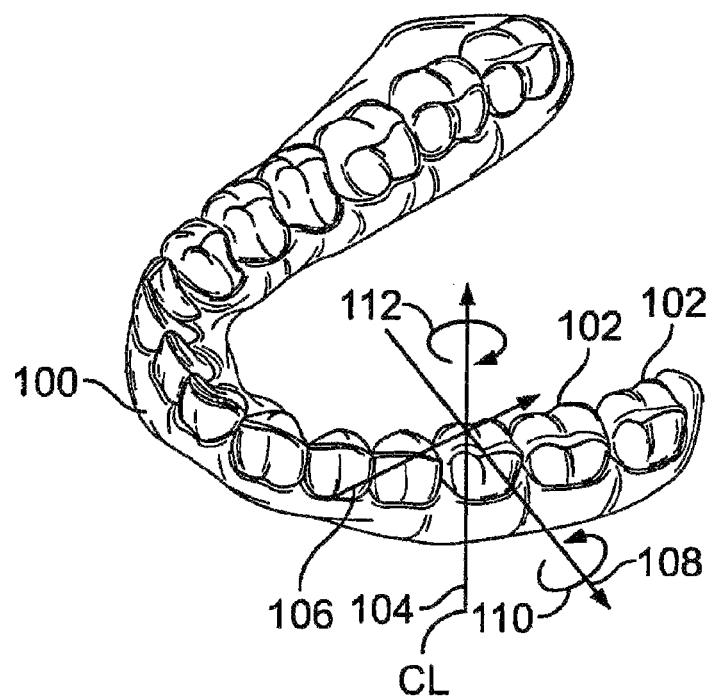
FIG. 2A illustrates in more detail the patient's lower jaw and provides a general indication of how teeth may be moved according to an embodiment of the present invention.

Referring now to FIG. 2A, the lower jaw 100 includes a plurality of teeth 102, for example, At least some of these teeth may be moved from an initial tooth arrangement to a final tooth arrangement. As a frame of reference describing how a tooth may be moved, an arbitrary centerline (CL) may be drawn through the tooth 102. With reference to this centerline (CL), each tooth may-be moved in orthogonal directions represented by axes 104, 106, and 108 (where 104 is the centerline). The centerline may be rotated about the axis 108 (root angulation) and the axis 104 (torque) as indicated by arrows 110 and 112, respectively. Additionally, the tooth may be rotated about the centerline, as represented by an arrow 112. Thus, all possible free-form motions of the tooth can be performed.

Figure 2B:
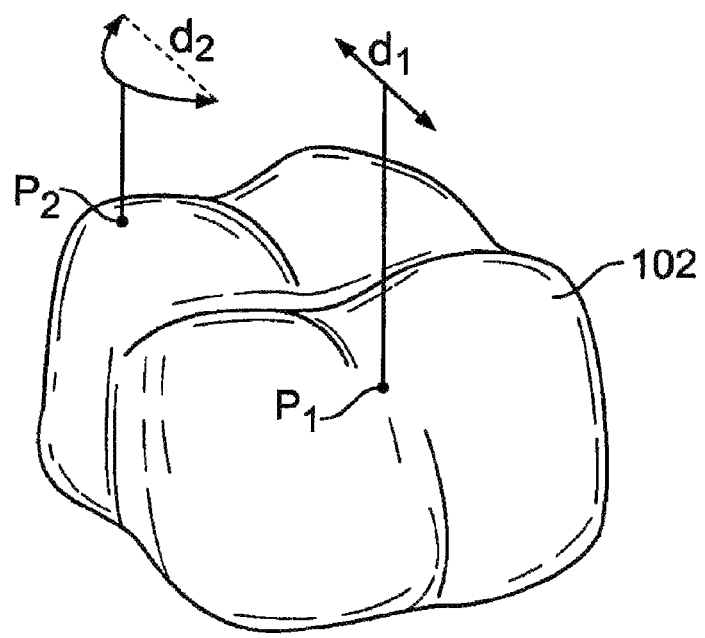
FIG. 2B illustrates a single tooth from FIG. 2A and defines determination of tooth movement distance according to an embodiment of the present invention.

FIG. 2B shows how the magnitude of any tooth movement may be defined in terms of a maximum linear translation of any point P on a tooth 102. Each point P1 will undergo a cumulative translation as that tooth is moved in any of the orthogonal or rotational directions defined in FIG. 2A. That is, while the point will usually follow a nonlinear path, there is a linear distance between any point in the tooth when determined at any two times during the treatment. Thus, an arbitrary point P1 may in fact undergo a true side-to-side translation as indicated by arrow d1, while a second arbitration point P2 may travel along an accurate path, resulting in a final translation d2. Many aspects of the present invention are defined in terms of the maximum permissible movement of a point P1 induced on any particular tooth. Such maximum tooth movement, in turn, is defined as the maximum linear translation of that point P1 on the tooth that undergoes the maximum movement for that tooth in any treatment step.

Figure 2C:
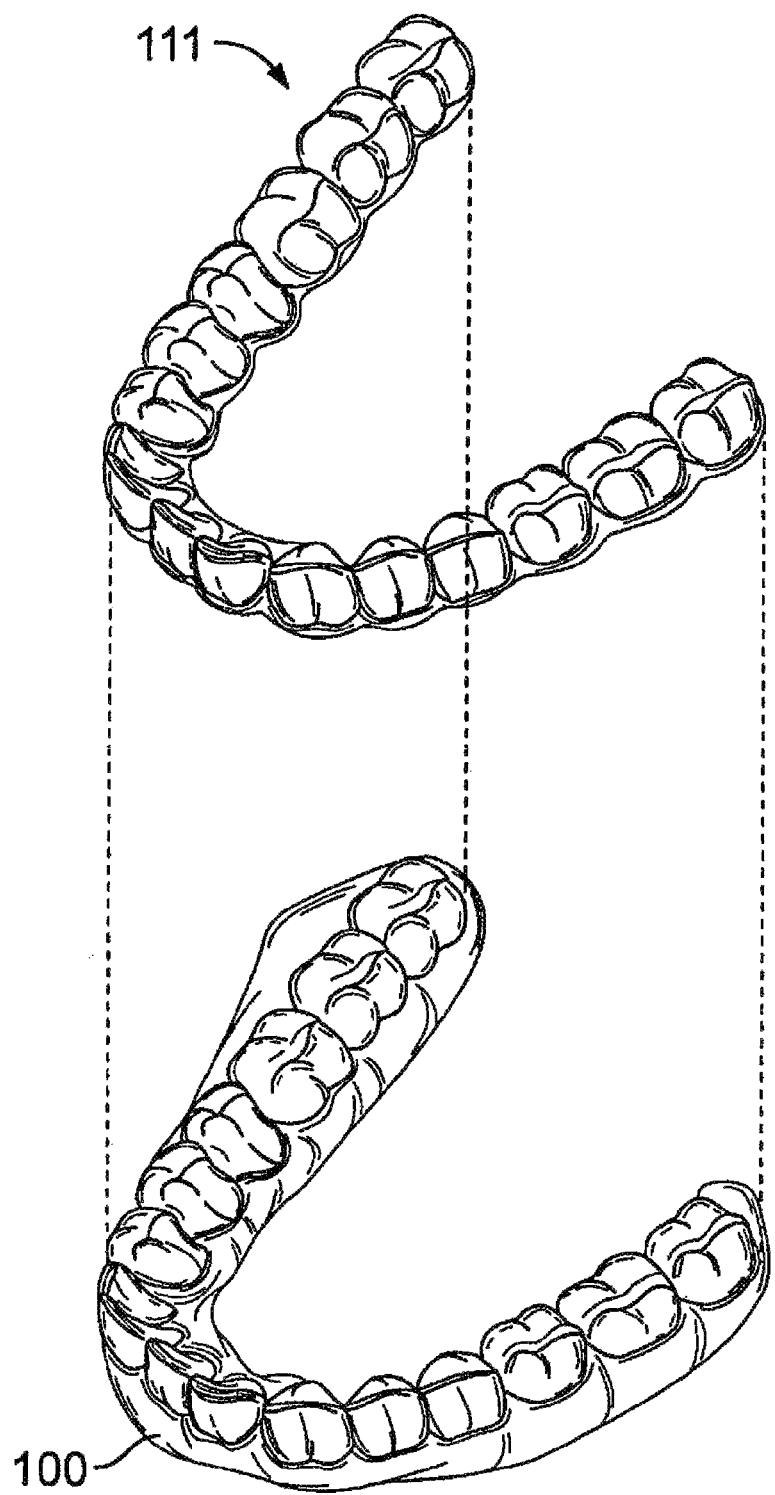
FIG. 2C illustrates the jaw of FIG. 2A together with an incremental positioning adjustment appliance according to an embodiment of the present invention.

FIG. 2C shows one adjustment appliance 111 which is worn by the patient in order to achieve an incremental repositioning of individual teeth in the jaw as described generally above. The appliance can include a shell (e.g., polymeric shell) having teeth-receiving cavities that receive and resiliently reposition the teeth. Such appliances, including those utilized in the Invisalign® System, are described in numerous patents and patent applications assigned to Align Technology, Inc. including, for example in U.S. Pat. Nos. 6,450,807, and 5,975,893, as well as on the company's website, which is accessible on the World Wide Web (see, e.g., the url "align.com").

As set forth in the prior applications, each appliance may be configured so that its tooth-receiving cavity has a geometry corresponding to an intermediate or final tooth arrangement intended for the appliance. The patient's teeth are progressively repositioned from their initial tooth arrangement to a final tooth arrangement by placing a series of incremental position adjustment appliances over the patient's teeth. The adjustment appliances can be generated all at the same stage or in sets or batches, e.g., at the beginning of a stage of the treatment, and the patient wears each appliance until the pressure of each appliance on the teeth can no longer be felt or has resulted in the maximum allowable tooth movement for that given stage. A plurality of different appliances (e.g., set) can be designed and even fabricated prior to the patient wearing any appliance of the plurality. At that point, the patient replaces the current appliance with the next appliance in the series until no more appliances remain. The appliances are generally not affixed to the teeth and the patient may place and replace the appliances at any time during the procedure. The final appliance or several appliances in the series may have a geometry or geometries selected to overcorrect the tooth arrangement, i.e., have a geometry which would (if fully achieved) move individual teeth beyond the tooth arrangement which has been selected as the "final." Such over-correction may be desirable in order to offset potential relapse after the repositioning method has been terminated, i.e., to permit movement of individual teeth back toward their pre-corrected positions. Over-correction may also be beneficial to speed the rate of correction, i.e., by having an appliance with a geometry that is positioned beyond a desired intermediate or final position, the individual teeth will be shifted toward the position at a greater rate. In such cases, the use of an appliance can be terminated before the teeth reach the positions defined by the appliance.

Figure 3:
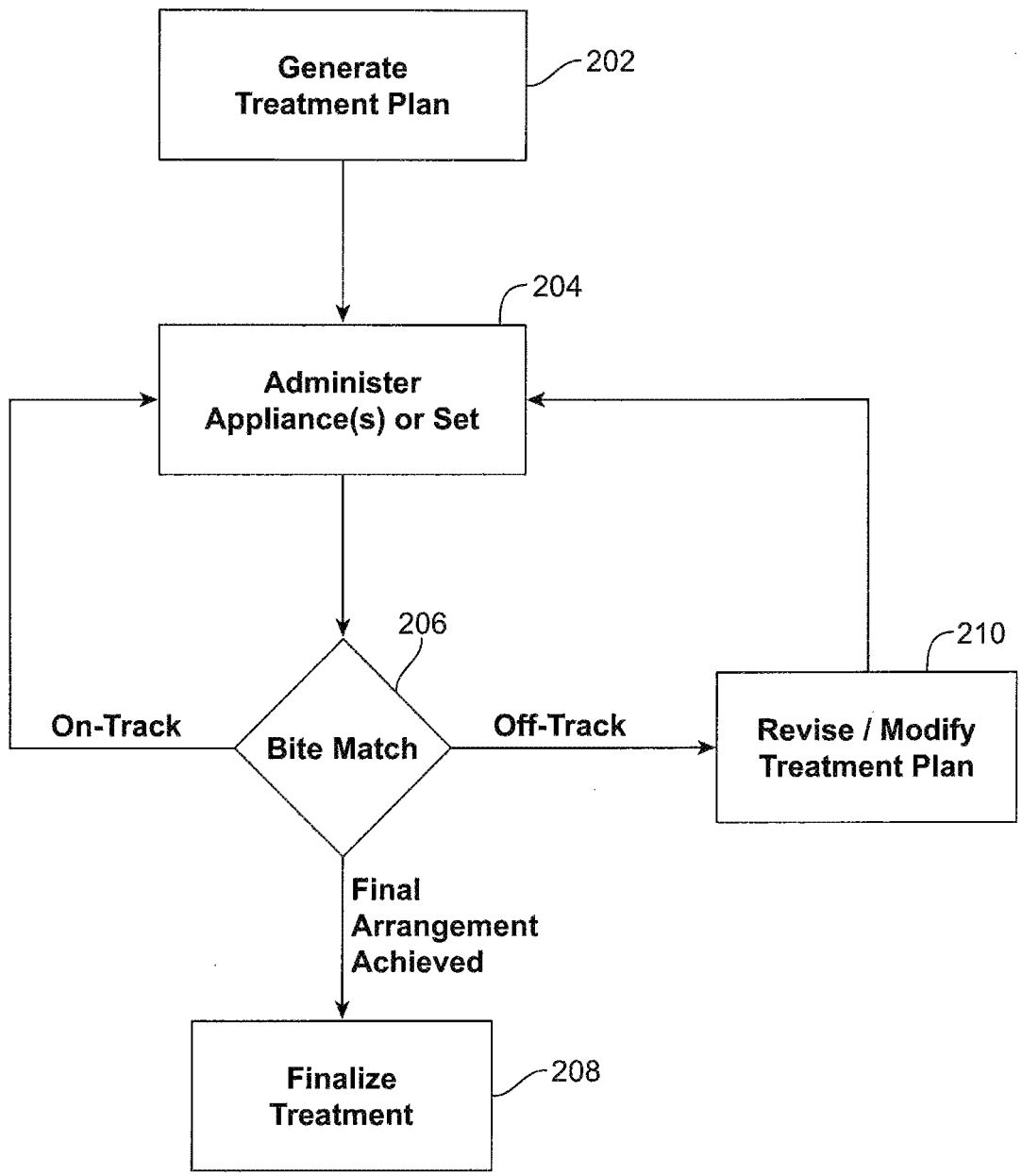
FIG. 3 shows generating and administering treatment according to an embodiment of the present invention.

Referring to FIG. 3, a method 200 according to the present invention is illustrated. Individual aspects of the process are discussed in further detail below. The process includes generating a treatment plan for repositioning a patient's teeth (Step 202). Briefly, a treatment plan will include obtaining data comprising an initial arrangement of the patient's teeth, which typically includes obtaining an impression or scan of the patient's teeth prior to the onset of treatment. The treatment plan will also include identifying a final or target arrangement of the patient's teeth that is desired, as well as a plurality of planned successive or intermediary tooth arrangements for moving the teeth along a treatment path from the initial arrangement toward the selected final or target arrangement. Appliances can be generated based on the planned arrangements and administered to the patient (Step 204). The appliances are typically administered in sets or batches of appliances, such as sets of 2, 3, 4, 5, 6, 7, 8, 9, or more appliances, but are not limited to any particular administrative scheme. After the treatment plan begins and following administration of appliances to the patient, teeth matching is done to assess a current and actual arrangement of the patient's teeth compared to a planned arrangement (Step 206). If the patient's teeth are determined to be "on-track" and progressing according to the treatment plan, then treatment progresses as planned. If the patient's teeth have reached the initially planned final arrangement, then treatment progresses to the final stages of treatment (Step 208). Where the patient's teeth are determined to be tracking according to the treatment plan, but have not yet reached the final arrangement, the next set of appliances can be administered to the patient (repeat Step 204, according to the initial Treatment Plan). If, on the other hand, the patient's teeth are determined at the teeth matching step (Step 206) not to be tracking with the treatment plan, then treatment is characterized as "off-track" and an assessment is made as to how further treatment of the patient will proceed. Typically, a revised treatment plan will be generated (Step 210), and may be selected, for example, to reposition the teeth from the current position to a final position, which may be the same destination as the initially determined final position according to the initial treatment plan.

Systems of the present invention can include network based systems, including a data network and a server terminal operatively coupled to the network. One or more client terminals can be included and operatively coupled to the network. Systems can optionally include more stand-alone or non-network based systems, including computers and software packages designed to at least partially operate independent of a data network and in which various steps of the currently described methods can be accomplished in an automated fashion at a remote location (e.g., practitioner's office).

Figure 4:
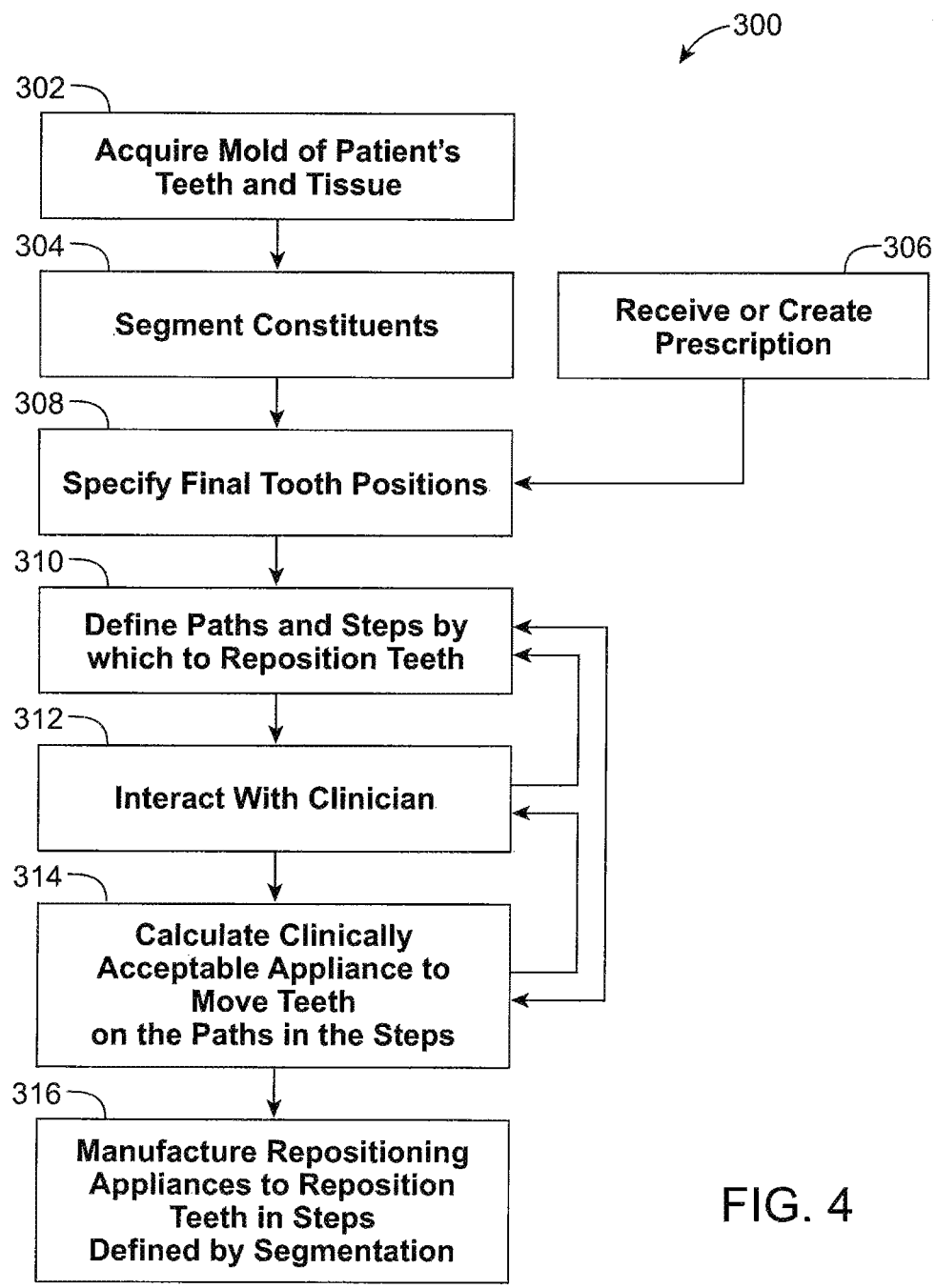
FIG. 4 illustrates generating a treatment plan according to an embodiment of the present invention.

FIG. 4 illustrates the general flow of an exemplary process 300 for defining and generating a treatment plan, including repositioning appliances for orthodontic treatment of a patient. The process 300 includes the methods, and is suitable for the apparatus, of the present invention, as will be described. The steps of the process can be implemented as computer program modules for execution on one or more computer systems.

As an initial step, a mold or a scan of patient's teeth or mouth tissue is acquired (Step 302). This generally involves taking casts of the patient's teeth and gums, and may in addition or alternately involve taking wax bites, direct contact scanning, x-ray imaging, tomographic imaging, sonographic imaging, and other techniques for obtaining information about the position and structure of the teeth, jaws, gums and other orthodontically relevant tissue. From the data so obtained, a digital data set is derived that represents an initial (e.g., pretreatment) arrangement of the patient's teeth and other tissues.

The initial digital data set, which may include both raw data from scanning operations and data representing surface models derived from the raw data, is processed to segment the tissue constituents from each other (Step 304), including defining discrete dental objects. For example, data structures that digitally represent individual tooth crowns can be produced. In some embodiments, digital models of entire teeth are produced, including measured or extrapolated hidden surfaces and root structures.

Desired final position of the teeth, or tooth positions that are desired and/or intended end result of orthodontic treatment, can be received, e.g., from a clinician in the form of a descriptive prescription, can be calculated using basic orthodontic prescriptions, or can be extrapolated computationally from a clinical prescription (Step 306). With a specification of the desired final positions of the teeth and a digital representation of the teeth themselves, the final position and surface geometry of each tooth can be specified (Step 308) to form a complete model of the teeth at the desired end of treatment. The result of this step is a set of digital data structures that represents a desired and/or orthodontically correct repositioning of the modeled teeth relative to presumed-stable tissue. The teeth and surrounding tissue are both represented as digital data.

Having both a beginning position and a final target position for each tooth, the process next defines a treatment path or tooth path for the motion of each tooth (Step 310). This includes defining a plurality of planned successive tooth arrangements for moving teeth along a treatment path from an initial arrangement to a selected final arrangement. In one embodiment, the tooth paths are optimized in the aggregate so that the teeth are moved in the most efficient and clinically acceptable fashion to bring the teeth from their initial positions to their desired final positions.

At various stages of the process, the process can include interaction with a clinician responsible for the treatment of the patient (Step 312). Clinician interaction can be implemented using a client process programmed to receive tooth positions and models, as well as path information from a server computer or process in which other steps of process 300 are implemented. The client process is advantageously programmed to allow the clinician to display an animation of the positions and paths and to allow the clinician to reset the final positions of one or more of the teeth and to specify constraints to be applied to the segmented paths.

The tooth paths and associated tooth position data are used to calculate clinically acceptable appliance configurations (or successive changes in appliance configuration) that will move the teeth on the defined treatment path in the steps specified (Step 314). Each appliance configuration corresponds to a planned successive arrangement of the teeth, and represents a step along the treatment path for the patient. The steps are defined and calculated so that each discrete position can follow by straight-line tooth movement or simple rotation from the tooth positions achieved by the preceding discrete step and so that the amount of repositioning required at each step involves an orthodontically optimal amount of force on the patient's dentition. As with other steps, this calculation step can include interactions with the clinician (Step 312).

Having calculated appliance definitions, the process 300 can proceed to the manufacturing step (Step 316) in which appliances defined by the process are manufactured, or electronic or printed information is produced that can be used by a manual or automated process to define appliance configurations or changes to appliance configurations. Appliances according to the treatment plan can be produced in entirety, such that each of the appliances are manufactured (e.g., prior to treatment), or can be manufactured in sets or batches. For example, in some cases in might be appropriate to manufacture an initial set of appliances at the outset of treatment with the intention of manufacturing additional sets of appliances (e.g., second, third, fourth, etc.) after treatment has begun (e.g., as discussed further herein). For example, a first set of appliances can be manufactured and administered to a patient. Following administration, it may be desirable to track the progression of the patient's teeth along the treatment path before manufacturing and/or administering subsequent set(s) of appliances.

Generating and/or analyzing digital treatment plans, as discussed herein, can include, for example, use of 3-dimensional orthodontic treatment planning tools such as ClinCheck from Align Technology, Inc. or other software available from eModels and OrthoCAD, among others. These technologies allow the clinician to use the actual patient's dentition as a starting point for customizing the treatment plan. The ClinCheck technology uses a patient-specific digital model to plot a treatment plan, and then uses a processed (e.g., segmented) scan of the achieved treatment outcome to assess the degree of success of the outcome as compared to the original digital treatment plan as, as discussed in U.S. Pat. Nos. 7,156,661 and 7,077,647 (see also, below).

In some cases, patients do not progress through treatment as expected and/or planned. For example, in some instances a patient's progression along a treatment path can become "off-track" or will deviate from an initial treatment plan, whereby an actual tooth arrangement achieved by the patient will differ from the expected or planned tooth arrangement, such as a planned tooth arrangement corresponding to the shape of a particular appliance. A determination that the progression of a patient's teeth is deviating or not tracking with the original treatment plan can be accomplished in a variety of ways. As set forth above, off-track deviations can be detected by visual and/or clinical inspection of the patient's teeth. For example, a substantial off track deviation from the expected or planned treatment may become apparent when the patient tries to wear a next appliance in a series. If the actual tooth arrangement substantially differs from the planned arrangement of the teeth, the next appliance will typically not be able to seat properly over the patient's teeth. Thus, an off-track deviation may become substantially visually apparent to a treating professional, or even to the patient, upon visual or clinical inspection of the teeth.

Detecting deviations from a planned treatment, however, can be difficult, particularly for patients as well as certain dental practitioners, such as those with more limited experience in orthodontics, certain general dentist, technicians and the like. Additionally, deviations that have progressed to the point that they are visually detectable clinically are often substantially off track with respect to the planned treatment, and earlier means of off-track detection is often desired. Thus, detecting deviations from a treatment plan can also be accomplished by comparing digital models of the patients teeth, and can often detect deviations from a treatment plan before the deviation becomes substantially apparent by visual or clinical inspection.

Figure 5:
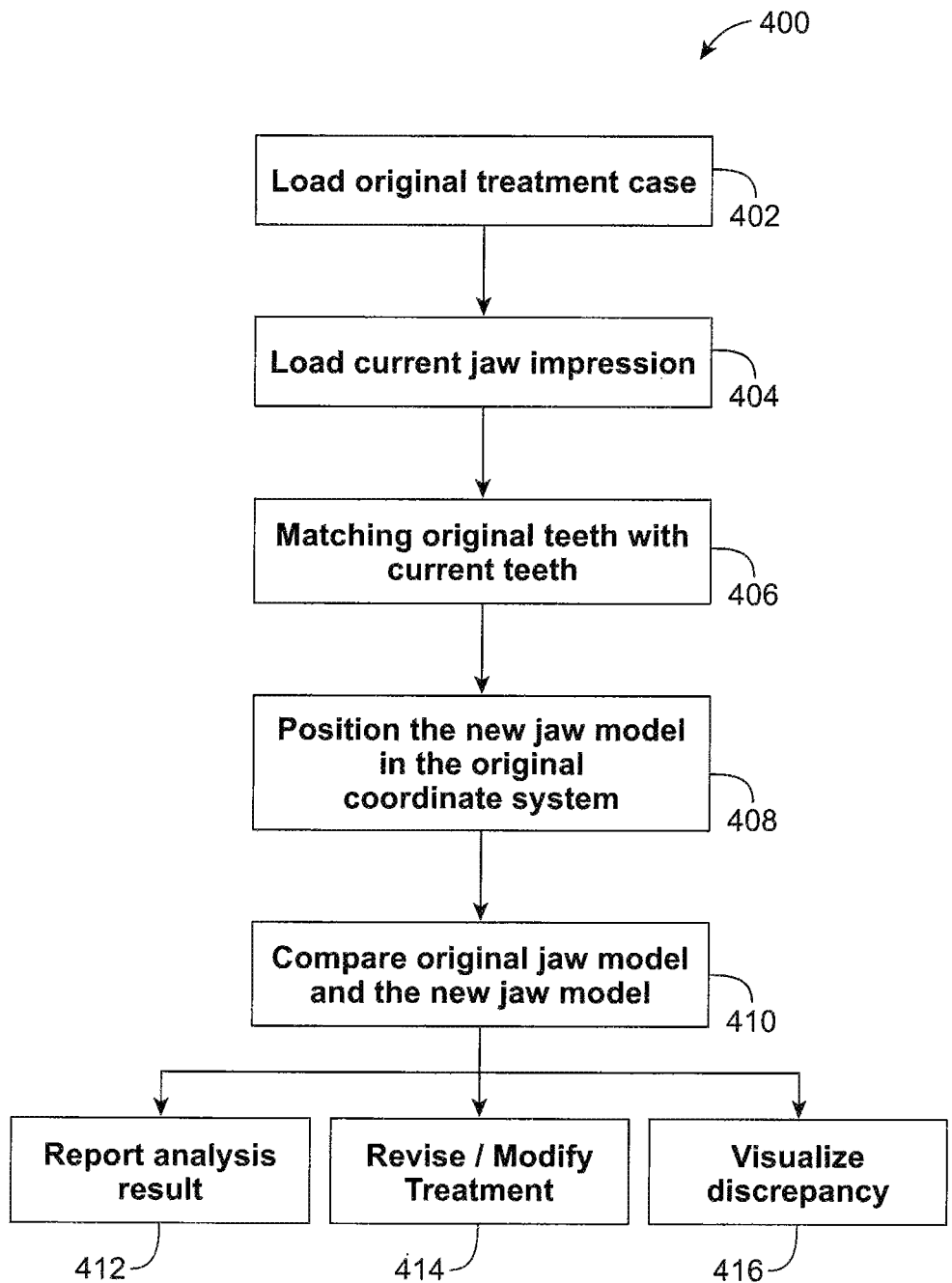
FIG. 5 illustrates a process including teeth matching according to one embodiment of the present invention.

An exemplary computer based teeth matching process according to an embodiment of the present invention is described with reference to FIG. 5. First, data from an earlier treatment plan is received (Step 402). Typically, data includes the initial data set or image data representing the patient's teeth in the original, pre-treatment positions, the initially identified final position, as well as planned intermediate or successive arrangements selected for moving teeth along the initial treatment path from the initial arrangement to the selected final arrangement. Next, a current jaw impression or data including a digital representation of the teeth in their current positions, after treatment has begun, is received and loaded (Step 404). Data including planned arrangements of the teeth are then compared to data including a representation of the patient's teeth in their current positions for an initial determination of whether a match exists (Step 406). Next, the new jaw data is segmented and positioned in the original coordinate system (Step 408). The process then compares the original jaw data against the new jaw data (Step 410). Based on the comparison, the process generates an analysis report (Step 412), new/revised treatment options or plans (Step 414), and/or allows visualization of any detected discrepancy (Step 416). See also, e.g., U.S. Pat. Nos. 7,156,661 and 7,077,647, for discussion of comparing actual position of the teeth relative to a planned or expected position using a processed (e.g., segmented) scan of the teeth positions following initiation of treatment.

In some instances, detecting a deviation from a treatment plan via comparison between digital models of the patients teeth can include comparing a current scan or image, which has not been segmented, of the patients teeth in a position after treatment has begun to a previously segmented data set of the patients teeth at a current, past or future stage. Use of an unsegmented, rather than segmented, digital representation of the current teeth positions may be desirable, for example, in order to avoid resource and/or labor intensive processing steps to transform the current unsegmented digital teeth model to a segmented digital teeth model. In addition, lower resolution or quality scans or images can save cost and time if the necessary reference points can be identified on the unsegmented current scan or image.

Figure 6:
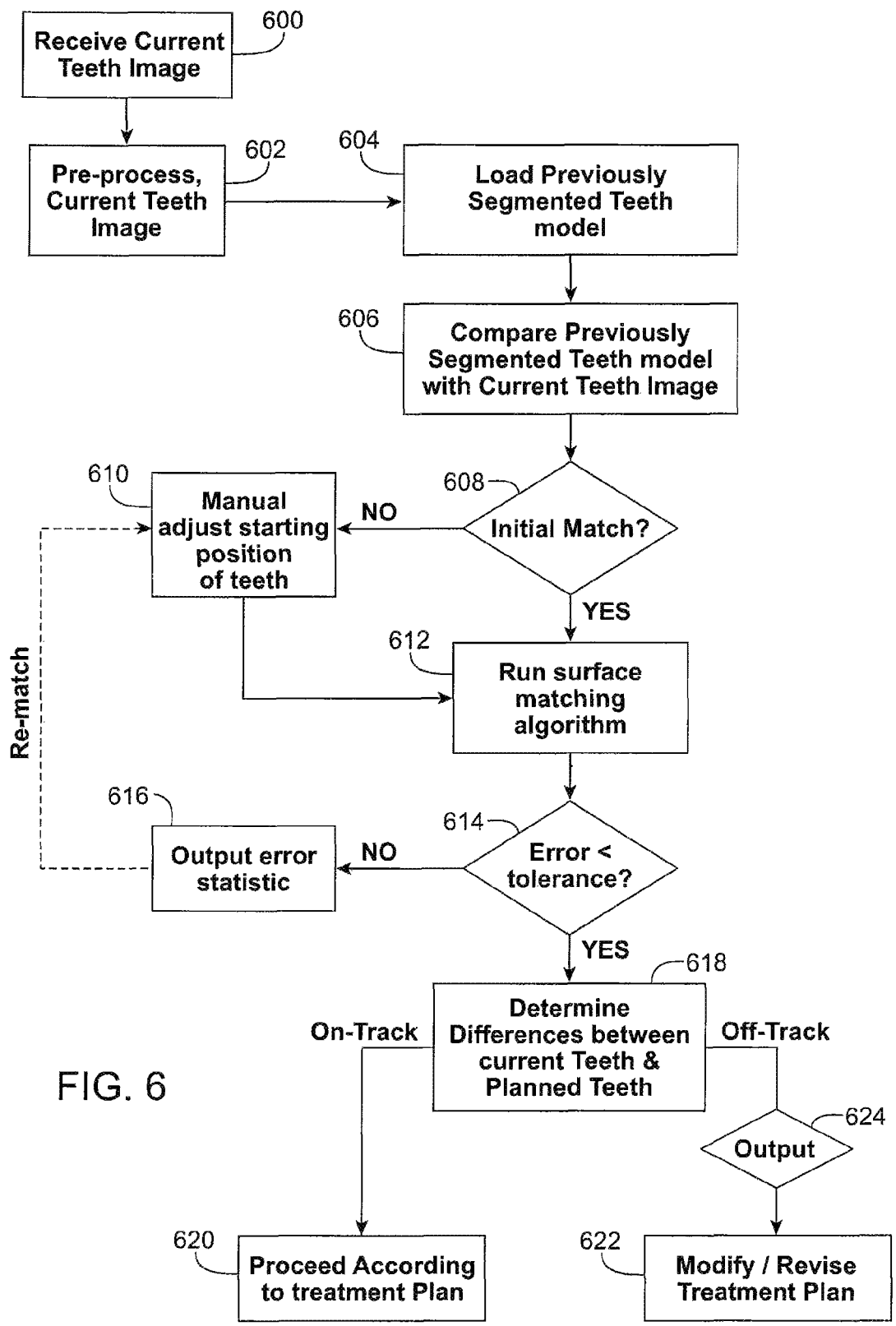
FIG. 6 shows a process including teeth matching according to another embodiment of the present invention.

FIG. 6 is a flow chart showing the steps of correcting deviations from a planned course of treatment to gradually reposition teeth, according to one embodiment of the present disclosure. The process starts in step 600, when current jaw data or "Current Teeth Image" is received. The current jaw data includes data representing an actual arrangement of the patients teeth following administration of appliances according to the original treatment plan. In step 602, the Current Teeth Image is pre-processed using a digital data tool (DDT) such that each tooth is assigned a Facial Axis of the Clinical Crown (FACC), i.e. a unique current identifier, with jaw characteristics set. Typically, according to the described embodiment, the Current Teeth Image does not need to be segmented, which saves a technician's time and hence overall cost.

In step 604, a Previously Segmented Teeth Model is selected, and is input into a system of the present invention for analysis and comparison with the Current Teeth Image. The Previously Segmented Teeth Model selected can include an Initially Segmented Teeth Model or a digital model of the patient's teeth in their initial, pre-treatment positions, the initial final position according to the initial or previous treatment plan (e.g., Prescribed Tooth Arrangement), or a planned successive tooth arrangement therebetween.

In step 606, the Previously Segmented Teeth Model and the Current Teeth Image are compared. This step includes a sort of "rough match" of the segmented model and the Current Teeth Image to identify corresponding features of the two models that may be compared (Step 608). For example, an initial matching algorithm can be executed which matches unique starting identifiers (FACCs) of each tooth in the Previously Segmented Teeth Model to the respective unique current identifiers (FACCs) of each tooth in the Current Teeth Image. The images can be overlaid on each other and the relative location of each tooth identified by its unique identifier (or FACC) to determine if there are any mismatches in step 608.

If any mismatches are found, an initial match has not occurred and the mismatches are displayed in the form of an informational dialog that provides details of the mismatches, such as teeth numbering irregularities or missing FACCs. A mismatch can occur, for example, if there are any teeth numbering irregularities, such as the total number of teeth in each model is not the same, or at least one tooth is missing a FACC. Mismatches may result, for example, where substantial dental work or reconstruction (e.g., tooth extraction, tooth reconstruction, filling, etc.) has occurred following the initial treatment plan or generation of Previously Segmented Teeth Model.

In Step 610, initial mismatch errors as identified above can be manually accounted for in the process. For example, a technician can manually adjust or reposition each tooth with a mismatch using the Previously Segmented Teeth Model or adjusts the information relating to each tooth with a mismatch (e.g., accounting for an extracted tooth).

If no mismatches are generated in step 608, or where mismatches have been accounted for according to 610, then an initial match occurs and the process moves to step 612. The initial match confirms that the technician is using the correct Previously Segmented Teeth Model and the Current Teeth Image, which provides a good starting point for executing a surface matching algorithm.

In step 612, more detailed matching and comparison between Previously Segmented Teeth Model and the Current Teeth Image occurs, which includes execution a surface matching algorithm. The surface matching algorithm can take a number of samples of each tooth in the Previously Segmented Teeth Model and finds the closest corresponding sampling point on the Current Teeth Image. A grid is created on each tooth and the number of samples is randomly selected and then the grid is overlaid on the Current Teeth Image.

In step 614, any resulting errors from the surface matching algorithm are compared to predetermined tolerances to determine if the resulting errors are less than the predetermined tolerance. Error tolerances can account for potential differences in the models being compared that might impair meaningful comparison, such as errors due to typical variance between different scans or impressions, surface differences or fluctuations, and the like. If the resulting errors are greater than the pre-determined tolerance, then in step 616, error statistics for the surface matching algorithm are typically output to a display device and can be further redirected to a technician for manual input or correction as in step 610.

If the resulting errors are less than the pre-determined tolerance, in step 618, then matching and comparison of the Previously Segmented Teeth Model and the Current Teeth Image proceeds for a determination whether the actual arrangement of the patient's teeth deviates from the planned arrangement. In particular, a determination can be made as to whether positional differences exist, and to what degree, between the teeth in their current positions compared to the expected or planned positions. Positional differences may indicate whether the patient's teeth are progressing according to the treatment plan or if the patient's teeth are substantially off track. Various clinical and/or positional parameters can be examined and compared for a determination as to whether a patient's teeth are substantially on track or are deviating from an expected arrangement according to the treatment plan. For example, positional parameters examined can include tooth rotation, extrusion, intrusion, angulation, inclination, translation, and the like. Threshold values for differences in one or more positional parameters can be selected as being indicative of a significant or substantial difference in tooth position. Exemplary threshold values for various positional parameters, according to one embodiment of the invention are listed in Table 1 below. Detecting positional differences above the selected threshold value(s) indicates that the actual arrangement of the patients teeth substantially deviates from the planned arrangement to which the comparison is made.

TABLE 1

OFF TRACK PARAMETERS. The threshold difference values of a planned position of teeth to actual positions selected as indicating that a patient's teeth have progressed substantially off-track.

| Type Movement | Difference Actual/Planned |
|---|---|
| Rotations | |
| Upper central incisors | 9 deg |
| Upper lateral incisors | 11 deg |
| Lower incisors | 11 deg |
| Upper cuspids | 11 deg |
| Lower cuspids | 9.25 deg |
| Upper Bicuspids | 7.25 deg |
| Lower First Bicuspid | 7.25 deg |
| Lower Second Bicuspid | 7.25 deg |
| molars | 6 deg |
| Extrusion | |
| Anterior | 0.75 mm |
| Posterior | 0.75 mm |
| Intrusion | |
| Anterior | 0.75 mm |
| Posterior | 0.75 mm |
| Angulation | |
| Anterior | 5.5 deg |
| Posterior | 3.7 deg |
| Inclination | |
| Anterior | 5.5 deg |
| Posterior | 3.7 deg |
| Translation | |
| BL Anterior | 0.7 mm |
| BL Posterior Cuspids | 0.9 mm |
| MD Anterior | 0.45 mm |
| MD Cuspids | 0.45 mm |
| MD Posterior | 0.5 mm |

If the patient's teeth are determined to be on track by comparison of the teeth in their current positions with teeth in their expected or planned positions, then treatment can progress according to the existing or original treatment plan (Step 620). For example, a patient determined to be progressing on track can be administered one or more subsequent appliances according to the treatment plan, such as the next set of appliances. Treatment can progress to the final stages and/or can reach a point in the treatment plan where bite matching is repeated for a determination of whether the patient's teeth are progressing as planned or if the teeth are off track. If the patient's teeth are determined off track and deviating from the planned arrangement, then treatment according to the original treatment plan will be suspended. Typically, a modified or revised treatment plan will be generated where a patient's teeth are determined as being substantially off track (Step 622). Regardless of whether the patient's teeth are determined to be off track or progressing according to the treatment plan, the process can generate a report or analysis of the results, and/or visualize the comparison, including any detected discrepancy (Step 624). Any such product can be transmitted, for example, to a technician or treating professional, to the patient, or elsewhere.

Figure 7:
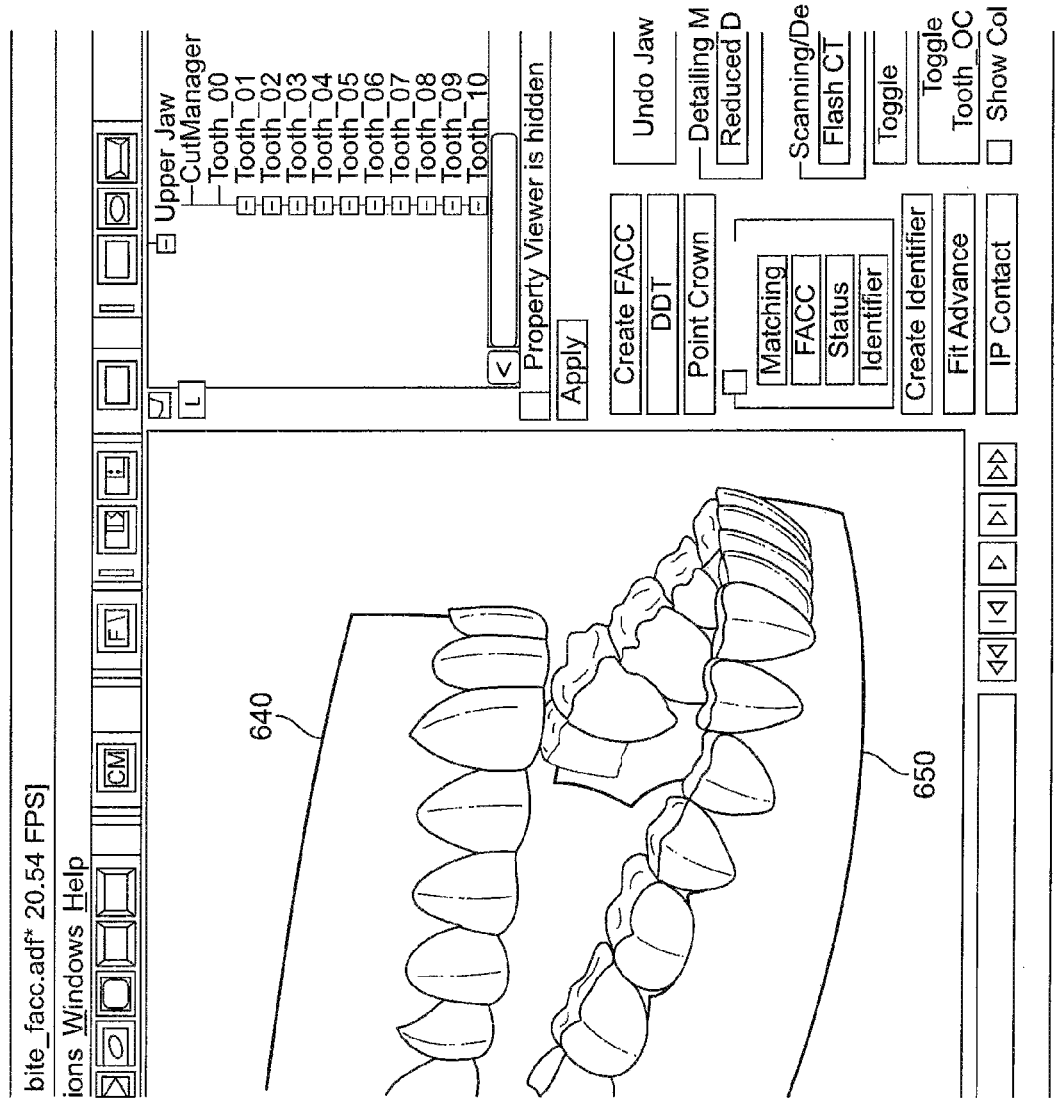
FIG. 7 is a screen shot showing a graphical representation of a three-dimensional model of a patient's upper and lower jaws based on a current digital data set representing teeth in their current positions, according to an embodiment of the present invention.

FIG. 7 is a screen shot showing a graphical representation of a three-dimensional model of a patient's upper and lower jaws 640, 650 generated from a Current Teeth Image. As described above, using a digital detailing tool (DDT), a technician pre-processes the Current Teeth Image by assigning and placing FACC's or unique current identifiers 74 on each tooth in the model. Unique current identifiers are landmarks on the teeth for the purposes of matching. Each FACC has a number associated with it and that is the tooth number, so the same tooth from the Previously Segmented Teeth Models and the Current Teeth Image should be in a similar location.

Figure 8:
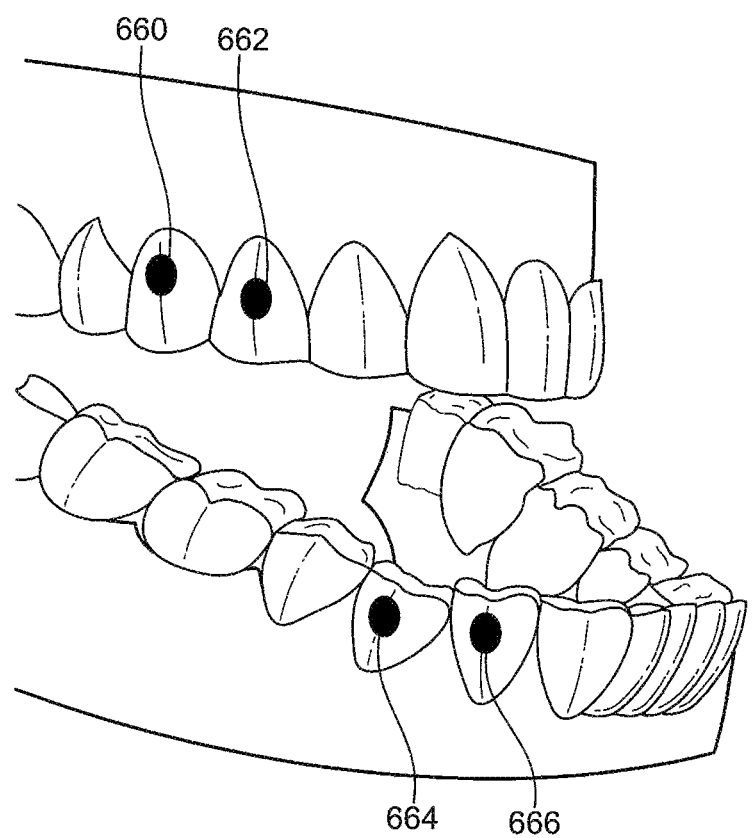
FIG. 8 is a graphical representation of a three-dimensional model of an initial match that can occur when the three dimensional model of digital translated images are overlaid on three dimensional model of the Current Teeth Image, according to one embodiment of the present invention.

FIG. 8 is a graphical representation of a three-dimensional model of a starting match that can occur when a Previously Segmented Teeth Model is overlaid on the Current Teeth Image, according to one embodiment of the present disclosure. The initial match provides a starting position for subsequent surface matching so that a good match is achieved.

If the initial matching algorithm determines that one or more teeth are mismatched, the initial matching algorithm cannot complete the initial matching satisfactorily because of teeth numbering irregularities or missing FACCs. In this instance, the initial matching algorithm will generate an informational dialog giving details of the mismatches allowing the technician to correct them and execute the initial matching algorithm again. Also shown in FIG. 8 are four attachments 660, 662, 664, 666 that have been optionally added to four of the patient's teeth.

See also, e.g., U.S. Pat. No. 8,075,306, entitled "System and Method for Detecting Deviations During the Course of an Orthodontic Treatment to Gradually Reposition Teeth," issued Dec. 13, 2011, the full disclosure of which is incorporated herein by reference, for further discussion of comparing an unsegmented representation of an actual arrangement of a patients teeth after treatment has begun, to a previously segmented model of the patient's teeth.

While the timing of the progress tracking steps described herein can be selected by the practitioner, typically at least general timing for conducting progress tracking measures of the present invention will be incorporated into the treatment plan and, therefore, will be pre-planned or planned at about the beginning of treatment or early on in the course of the patient's treatment (e.g., prior to the patient wearing a given set of appliances so as to reposition the teeth). Thus, in one embodiment of the invention, a treatment plan will include a prescribed timing for the planned tracking steps. The prescribed timing can include a specifically recommended date or may include a general increment of time (e.g., at treatment week 9, 10, 11, etc.), or can be based on the timing of other events of the treatment plan (e.g., after a patient wears a set of appliances).

Timing of progress tracking steps can be selected to occur based on a somewhat standardized treatment protocol or can be more particularly customized to an individual patient. More standardized protocols can take into account certain population statistics, generalized clinical expectations, and/or physiological parameters that can be used to generally predict rate of movement of a patient's teeth and the minimum length of treatment time necessary for the patient's teeth to progress off track if such progression is occurring. Clinical parameters can include, for example, root structure, including length, shape, and positioning, as well as certain jaw characteristics such as jaw bone density, patient age, gender, ethnicity, medications/health history profile, dental history including prior treatment with orthodontics, type of orthodontic treatment plan (extraction vs. non-extraction), and the like. Assuming a 2-week wear interval for each appliance, with a maximum tooth velocity of 0.25 mm/tooth per aligner, typically about 16 to 20 weeks of repositioning treatment (8 to 10 appliances) is required before movement of the teeth is substantial enough to detect a noncompliant or off track movement of the teeth, if such off track movement is occurring, though more drastic movements can produce off track movement after only a few weeks.

As set forth above, timing of tracking measures can be selected based on the particular movement(s) prescribed and/or characteristics of the patient being treated and, therefore, are said to be customized to the particular patient. For example, certain desired tooth movements in a treatment plan may be deemed either more unpredictable or at increased risk of moving off track and may require specifically timed tracking or monitoring. For example, for certain movements including, e.g., extrusions or rotations of round teeth (e.g., canines), more specific or frequent tracking may be desired. Additionally, certain physiological or clinical characteristics of the patient may be identified as indicating that particularly timed and/or frequency of tracking might be desired. Whether tracking is selected based on standardized protocols or more customized to the individual patient, tracking may or may not be selected to uniformly timed during the course of treatment. For example, a lower frequency of tracking measures may be desired or needed during certain portions or phases of treatment than others (e.g., space closure). Regardless of whether tracking timing is customized or more standardized, the selected timing will typically provide the additional advantage of efficiently planning tracking in the treatment plan to minimize unnecessary use of practitioner time and other resources.

Figure 9A:
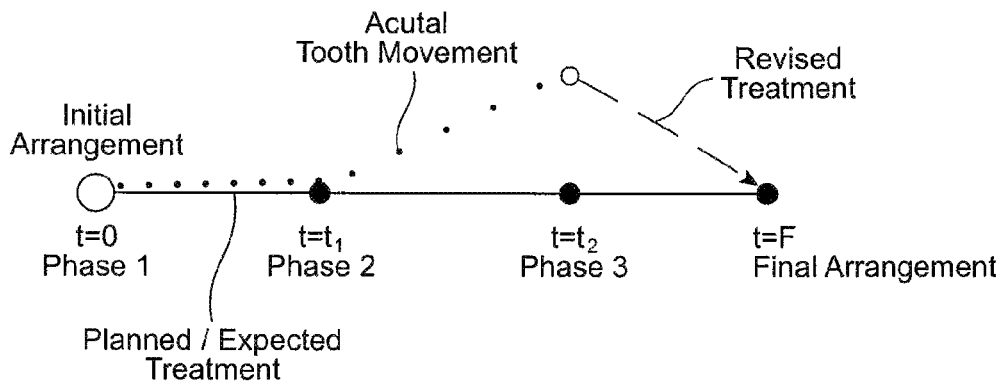
FIG. 9A through FIG. 9C show plurality of stages of teeth correction and revision of treatment, according to several embodiments of the present invention.
Figure 9B:
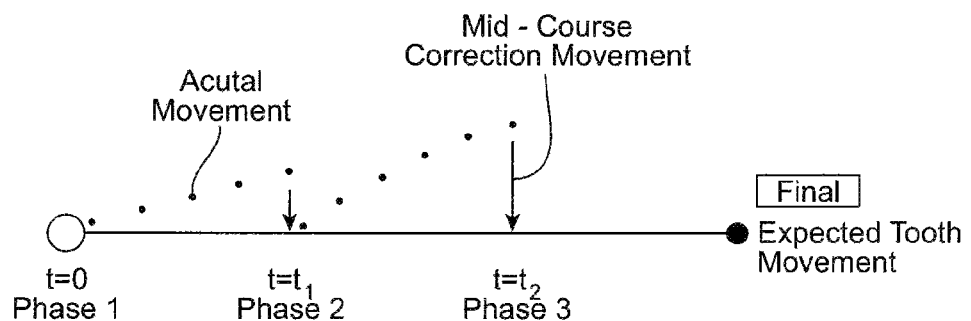
Figure 9C:
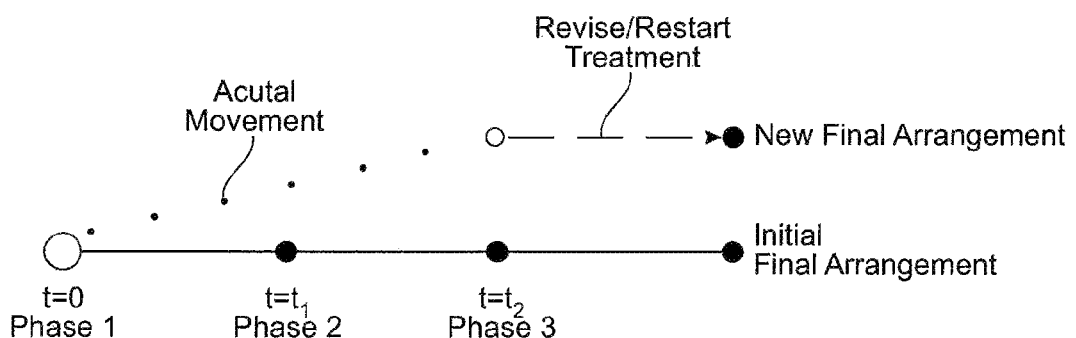

Once a determination is made that the patient's actual arrangement of teeth deviates from a planned arrangement and that the patient's teeth are not progressing as expected/planned, a change or correction in the course of treatment can be selected, for example, by generating a revised or modified treatment plan. Referring to FIGS. 9A-9C, revised treatment following determination that a patient's teeth are not progressing on track is described. As set forth above, a treatment plan includes a plurality of planned successive tooth arrangements for moving teeth along a treatment path from an initial arrangement to a selected final arrangement. The treatment plan, administration of sets of appliances to a patient according to the planned arrangements, can include a plurality of phases (1 through 4) where at time=0, the initial treatment plan begins. The initial treatment plan is illustrated by a solid line. Bite matching for a determination of whether a case is progressing "on track" or "off track", as described above (e.g., FIGS. 5, 6), can take place at one or more of the phases or points along the administration of treatment.

In particular, current tooth positions of the patient can be obtained from the patient any one or more phases and compared to segmented models of the patient's teeth according to an earlier or original treatment plan. Where teeth are determined to be deviating from the planned treatment plan or progressing "off track", as illustrated by broken lines, modification or revision of treatment plan can occur. In one embodiment, a revised treatment plan can include restaging the patient's treatment from the determined actual position to the originally determined final position (FIG. 9A). Revised treatment path (illustrated by dashed lines) can proceed directly toward the initially determined final position and need not attempt to redirect treatment back onto the original treatment path. In this case, while partial overlap/intersection of the revised treatment path with the original treatment path may occur, the revised treatment path will at least partially diverge from the initial treatment path and proceed directly toward the initially determined final arrangement of the teeth. Such an approach may be selected, for example, where retaining the initially determined final position is desired. This approach also advantageously permits use of the originally processed and segmented data, thereby allowing avoidance of costly processing steps.

Alternatively, a revised treatment plan can include a more direct "mid-course correction", in which the revised treatment plan includes a more direct path back toward the a planned arrangement of the initial treatment plan, as illustrated in FIG. 9B. While this approach may make use of the originally planned final arrangement, the more primary concern in this example type of correction is redirecting treatment back to the original treatment path, rather than from the actual position and more directly toward the original final position. In yet another embodiment, as illustrated in FIG. 9C, a revised treatment plan can include essentially "restarting" treatment, and generating a new final arrangement of the teeth, for example, from segmenting and staging a new impression of the teeth, and directing the patient's teeth from the actual arrangement to the newly determined final arrangement of the teeth.

Figure 10:
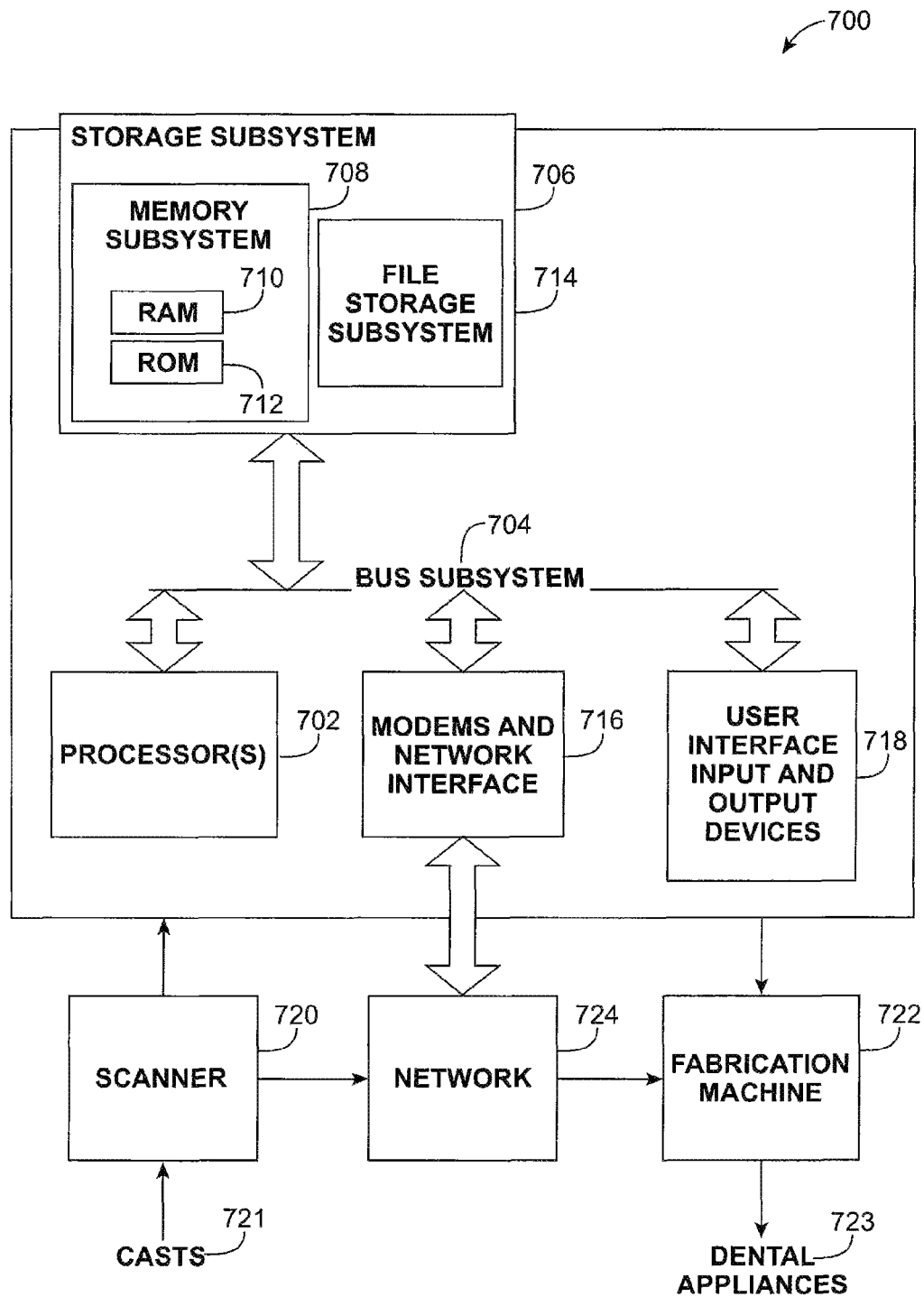
FIG. 10 is a block diagram illustrating a system for generating appliances in accordance with methods and processes of the present invention.

FIG. 10 is a simplified block diagram of a data processing system 700 that may be used in executing methods and processes described herein. The data processing system 700 typically includes at least one processor 702 that communicates with a number of peripheral devices via bus subsystem 704. These peripheral devices typically include a storage subsystem 706 (memory subsystem 708 and file storage subsystem 714), a set of user interface input and output devices 718, and an interface to outside networks 716, including the public switched telephone network. This interface is shown schematically as "Modems and Network Interface" block 716, and is coupled to corresponding interface devices in other data processing systems via communication network interface 724. Data processing system 700 can include, for example, one or more computers, such as a personal computer, workstation, mainframe, and the like.

The user interface input devices 718 are not limited to any particular device, and can typically include, for example, a keyboard, pointing device, mouse, scanner, interactive displays, etc. Similarly, various user interface output devices can be employed in a system of the invention, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically comprises memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the Internet's World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining an image of a patient's teeth (e.g., from casts 721), some of which have been described herein above, which can be obtained either from the patient or from treating professional, such as an orthodontist, and includes means of providing the image data/information to data processing system 700 for further processing. In some embodiments, scanner 720 may be located at a location remote with respect to other components of the system and can communicate image data and/or information to data processing system 700, for example, via a network interface 724. Fabrication system 722 fabricates dental appliances 723 based on a treatment plan, including data set information received from data processing system 700. Fabrication machine 722 can, for example, be located at a remote location and receive data set information from data processing system 700 via network interface 724.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for identifying and correcting deviations of a patient's teeth from an orthodontic treatment plan, the method comprising:

scanning a patient's teeth with a scanner to form an unsegmented three-dimensional (3D) model of a current tooth arrangement of the patient;

comparing, using one or more processors, a previously segmented 3D digital model of a target tooth arrangement specified by the orthodontic treatment plan to the unsegmented 3D digital model of a current tooth arrangement of the patient;

identifying, using one or more processors, a discrepancy between the current tooth arrangement and the target tooth arrangement based on the comparing; and generating, using one or more processors, a modified orthodontic treatment plan in response to the identified discrepancy.

2. The method of claim 1, wherein the comparing step comprises matching a surface of at least one tooth from the previously segmented 3D digital model to a surface of at least one corresponding tooth from the unsegmented 3D digital model.

3. The method of claim 1, wherein the comparing step comprises calculating at least one positional difference between at least one tooth of the current tooth arrangement and at least one corresponding tooth of the target tooth arrangement.

4. The method of claim 3, wherein the identifying step comprises determining that the at least one positional difference exceeds a predetermined threshold value.

5. The method of claim 1, wherein the orthodontic treatment plan comprises moving the patient's teeth along an initial treatment path from an initial tooth arrangement towards a subsequent tooth arrangement, and the modified orthodontic treatment plan comprises moving the patient's teeth along a revised treatment path from the current tooth arrangement directly towards the subsequent tooth arrangement.

6. The method of claim 1, wherein the orthodontic treatment plan comprises moving the patient's teeth along an initial treatment path from an initial tooth arrangement towards a subsequent tooth arrangement, and the modified orthodontic treatment plan comprises moving the patient's teeth from the current tooth arrangement towards a tooth arrangement specified by the initial treatment path.

7. The method of claim 1, wherein the orthodontic treatment plan comprises moving the patient's teeth along an initial treatment path from an initial tooth arrangement towards a first subsequent tooth arrangement, and the modified orthodontic treatment plan comprises moving the patient's teeth along a revised treatment path from the current tooth arrangement towards a second subsequent arrangement different from the first subsequent tooth arrangement.

8. A system for identifying and correcting deviations of a patient's teeth from an orthodontic treatment plan, the system comprising:

one or more processors; and memory, including instructions executable by the one or more processors to cause the system to at least:

scan a patient's teeth with a scanner to form an unsegmented three-dimensional (3D) model of a current tooth arrangement of the patient;

compare a previously segmented 3D digital model of a target tooth arrangement specified by the orthodontic treatment plan to the unsegmented 3D digital model of a current tooth arrangement of the patient, identify a discrepancy between the current tooth arrangement and the target tooth arrangement based on the comparing, and generate a modified orthodontic treatment plan in response to the identified discrepancy.

9. The system of claim 8, wherein the orthodontic treatment plan comprises moving the patient's teeth along an initial treatment path from an initial tooth arrangement towards a subsequent tooth arrangement, and the modified orthodontic treatment plan comprises moving the patient's teeth along a revised treatment path from the current tooth arrangement directly towards the subsequent tooth arrangement.

10. The system of claim 8, wherein the orthodontic treatment plan comprises moving the patient's teeth along an initial treatment path from an initial tooth arrangement towards a subsequent tooth arrangement, and the modified orthodontic treatment plan comprises moving the patient's teeth from the current tooth arrangement towards a tooth arrangement specified by the initial treatment path.

11. The system of claim 8, wherein the orthodontic treatment plan comprises moving the patient's teeth along an initial treatment path from an initial tooth arrangement towards a first subsequent tooth arrangement, and the modified orthodontic treatment plan comprises moving the patient's teeth along a revised treatment path from the current tooth arrangement towards a second subsequent arrangement different from the first subsequent tooth arrangement.

12. The system of claim 8, further comprising a user interface configured to receive user input indicating locations of at least one landmark on each tooth of the unsegmented 3D digital model.

13. The system of claim 12, wherein the at least one landmark comprises a facial axis of the clinical crown (FACC) identifier.

14. The system of claim 12, wherein the compare step comprises matching the at least one landmark on each tooth of the unsegmented 3D digital model to at least one corresponding landmark on each tooth of the previously segmented 3D digital model.

15. The system of claim 8, further comprising a user interface configured to display a visualization of the discrepancy between the current tooth arrangement and the target tooth arrangement to a user.

16. One or more non-transitory computer-readable storage media having stored thereon executable instructions that, when executed by one or more processors of a computer system for identifying and correcting deviations of a patient's teeth from an orthodontic treatment plan, cause the computer system to at least:

scan a patient's teeth with a scanner to form an unsegmented three-dimensional (3D) model of a current tooth arrangement of the patient;

compare a previously segmented 3D digital model of a target tooth arrangement specified by the orthodontic treatment plan to the unsegmented 3D digital model of a current tooth arrangement of the patient, identify a discrepancy between the current tooth arrangement and the target tooth arrangement based on the comparing, and generate a modified orthodontic treatment plan in response to the identified discrepancy.

17. The one or more non-transitory computer-readable storage media of claim 16, wherein the orthodontic treatment plan comprises moving the patient's teeth along an initial treatment path from an initial tooth arrangement towards a subsequent tooth arrangement, and the modified orthodontic treatment plan comprises moving the patient's teeth along a revised treatment path from the current tooth arrangement directly towards the subsequent tooth arrangement.

18. The one or more non-transitory computer-readable storage media of claim 16, wherein the orthodontic treatment plan comprises moving the patient's teeth along an initial treatment path from an initial tooth arrangement towards a subsequent tooth arrangement, and the modified orthodontic treatment plan comprises moving the patient's teeth from the current tooth arrangement towards a tooth arrangement specified by the initial treatment path.

19. The one or more non-transitory computer-readable storage media of claim 16, wherein the orthodontic treatment plan comprises moving the patient's teeth along an initial treatment path from an initial tooth arrangement towards a first subsequent tooth arrangement, and the modified orthodontic treatment plan comprises moving the patient's teeth along a revised treatment path from the current tooth arrangement towards a second subsequent arrangement different from the first subsequent tooth arrangement.

* * * * *